(12) United States Patent
Inoue et al.

(10) Patent No.: US 8,348,851 B2
(45) Date of Patent: Jan. 8, 2013

(54) BLOOD PRESSURE MEASUREMENT DEVICE AND CONTROL METHOD OF THE SAME

(75) Inventors: Kouichi Inoue, Ashigarakami-gun (JP); Osamu Tochikubo, Yokohama (JP)

(73) Assignees: Terumo Kabushiki Kaisha, Shibuya-Ku, Tokyo (JP); Public University Corporation Yokohama City University, Yokohama-Shi, Kanagawa (JP)

( * ) Notice: Subject to any disclaimer, the term of this patent is extended or adjusted under 35 U.S.C. 154(b) by 287 days.

(21) Appl. No.: 12/766,558

(22) Filed: Apr. 23, 2010

(65) Prior Publication Data
US 2010/0210957 A1    Aug. 19, 2010

Related U.S. Application Data

(63) Continuation of application No. PCT/JP2008/069055, filed on Oct. 21, 2008.

(30) Foreign Application Priority Data

Oct. 25, 2007    (JP) .................................. 2007-278069

(51) Int. Cl.
*A61B 5/02*    (2006.01)
(52) U.S. Cl. ........................................ 600/485; 600/493
(58) Field of Classification Search .................. 600/485, 600/493
See application file for complete search history.

(56) References Cited

U.S. PATENT DOCUMENTS

| | | | |
|---|---|---|---|
| 4,751,930 A | | 6/1988 | Terada et al. |
| 5,316,006 A | * | 5/1994 | Inage et al. ................... 600/494 |
| 5,533,511 A | * | 7/1996 | Kaspari et al. ................ 600/485 |
| 5,564,426 A | * | 10/1996 | Iwai .............................. 600/493 |
| 5,961,467 A | * | 10/1999 | Shimazu et al. .............. 600/485 |
| 2004/0181254 A1 | * | 9/2004 | Choi et al. ..................... 606/202 |
| 2008/0281168 A1 | * | 11/2008 | Gibson et al. ................. 600/301 |

(Continued)

FOREIGN PATENT DOCUMENTS

EP    1 125 546 A1    8/2001
(Continued)

OTHER PUBLICATIONS

International Search Report issued by the Japanese Patent Office on Nov. 11, 2008 as the International Searching Authority in International Application No. PCT/JP2008/069055.

(Continued)

*Primary Examiner* — Navin Natnithithadha
*Assistant Examiner* — Etsub Berhanu
(74) *Attorney, Agent, or Firm* — Buchanan Ingersoll & Rooney PC

(57) ABSTRACT

This invention provides a user with information by which the reliability of a measured blood pressure value can be determined. A blood pressure measurement device includes a cuff which presses a blood pressure measurement portion, a pressure control means for pressurizing or depressurizing the interior of the cuff, a pressure sensor which senses the internal pressure of the cuff, a pulse wave signal extracting means for extracting time-series data of a pulse wave signal superposed on the cuff internal pressure sensed by the pressure sensor, in the process in which the pressure control means pressurizes or depressurizes the cuff, and a display means for displaying a pulse waveform corresponding to a pulse wave signal of at least one period, together with the value of a cuff internal pressure corresponding to the pulse wave signal, based on the extracted pulse wave signal time-series data.

6 Claims, 15 Drawing Sheets

U.S. PATENT DOCUMENTS

2009/0312651 A1    12/2009   Sano et al.

FOREIGN PATENT DOCUMENTS

| | | | |
|---|---|---|---|
| JP | 62-014831 | A | 1/1987 |
| JP | 2-045034 | A | 2/1990 |
| JP | 2-25610 | A | 6/1990 |
| JP | 2-277433 | A | 11/1990 |
| JP | 6-292660 | A | 10/1994 |
| JP | 2000-079101 | A | 3/2000 |
| JP | 2000-287945 | A | 10/2000 |
| JP | 2004-344308 | A | 12/2004 |
| JP | 2007-167171 | A | 7/2007 |
| TW | 576727 | B | 2/2004 |

OTHER PUBLICATIONS

Non-English language of the Written Opinion issued by the Japanese Patent Office on Nov. 11, 2008 as the International Searching Authority in International Application No. JP2008/069055.

Office Action dated Dec. 7, 2011, issued in the corresponding Taiwanese Patent Application No. 097140749 (6 pages).

Japanese Office Action issued Mar. 2, 2012 by the Japanese Patent Office in Japanese Application No. 2007-278069 and English language translation thereof.

Official Action issued on Jul. 27, 2012 by the Taiwanese Patent Office in Taiwanese Patent Application No. 097140749, and English language translation.

* cited by examiner

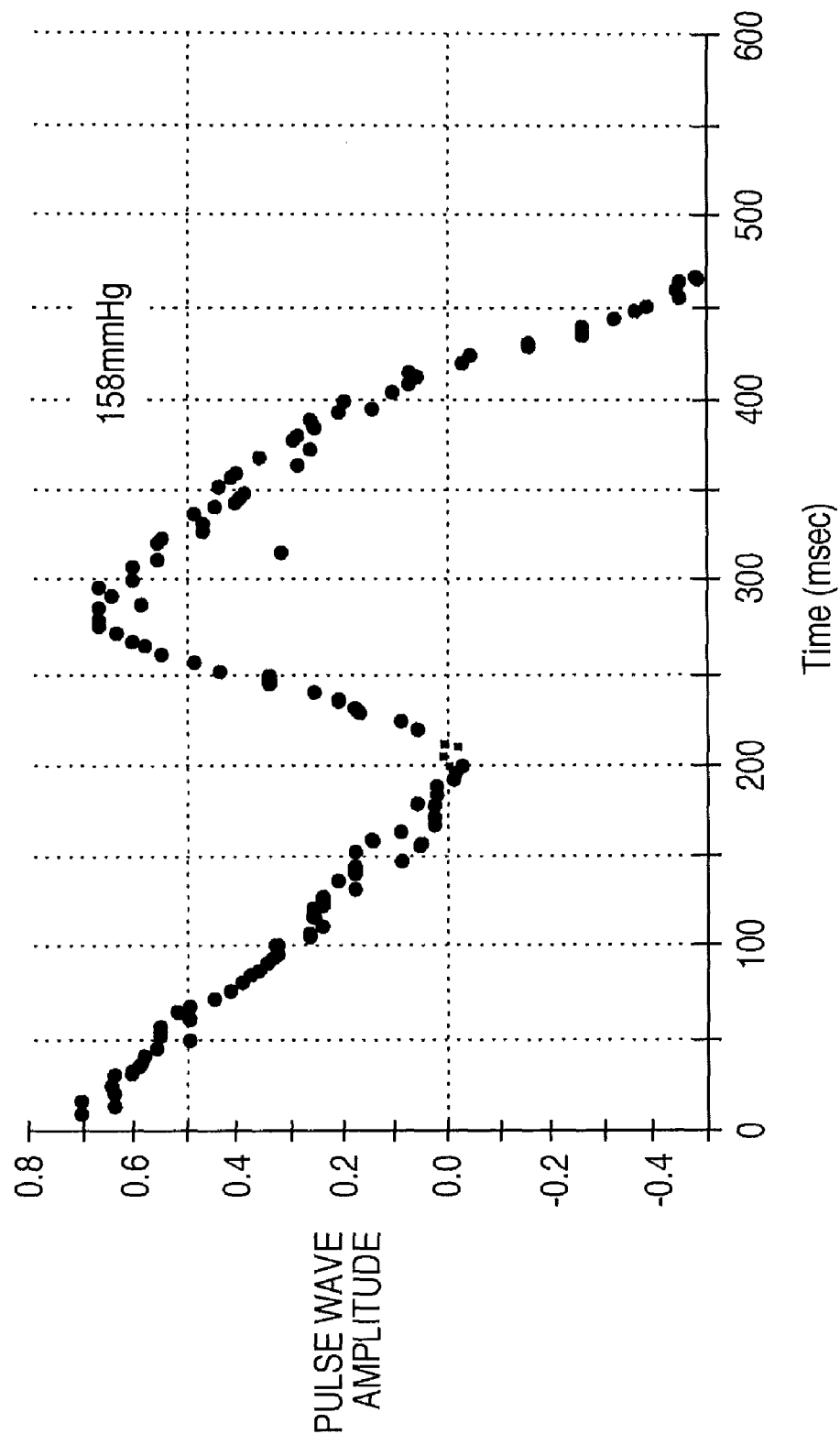

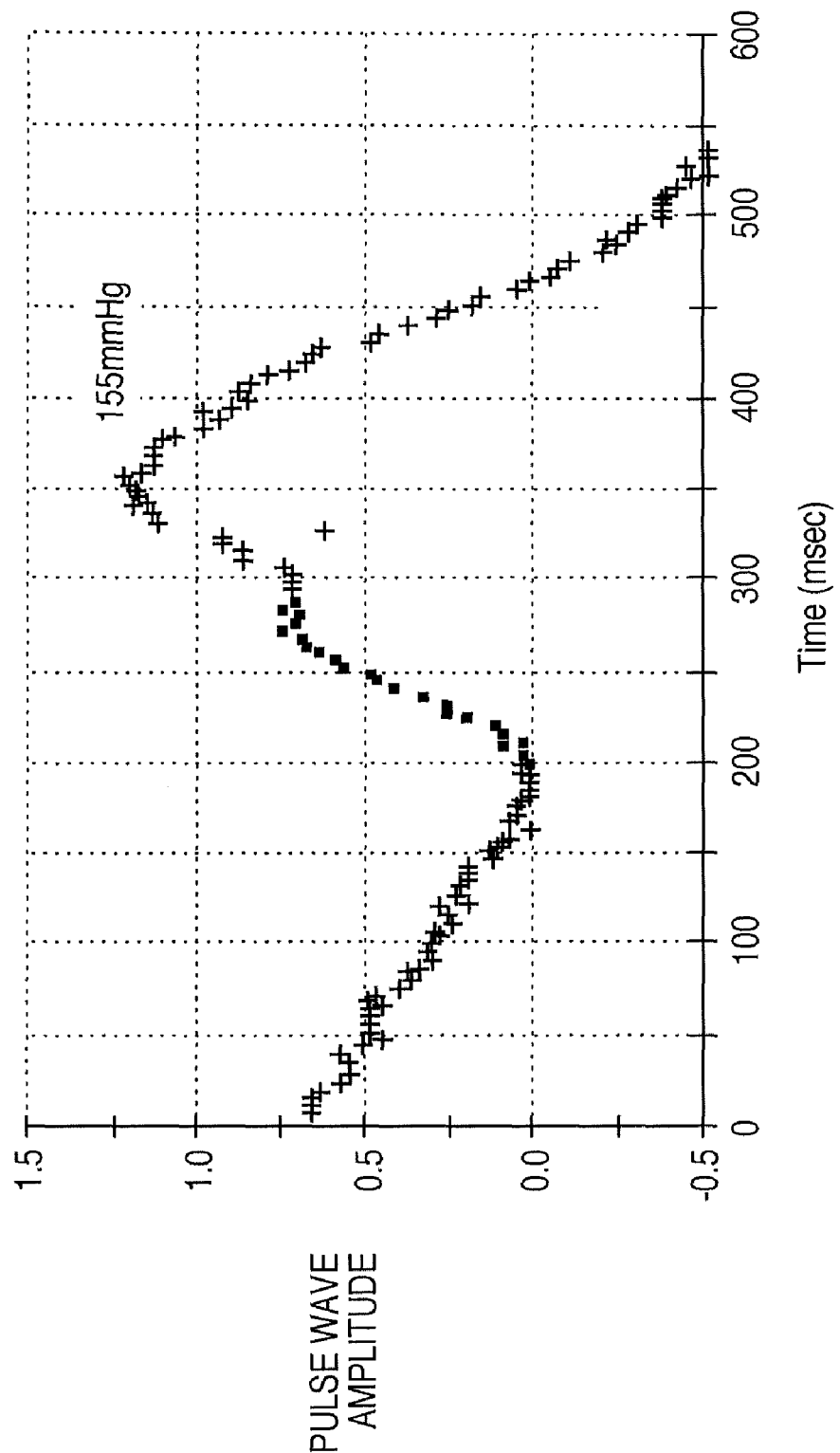

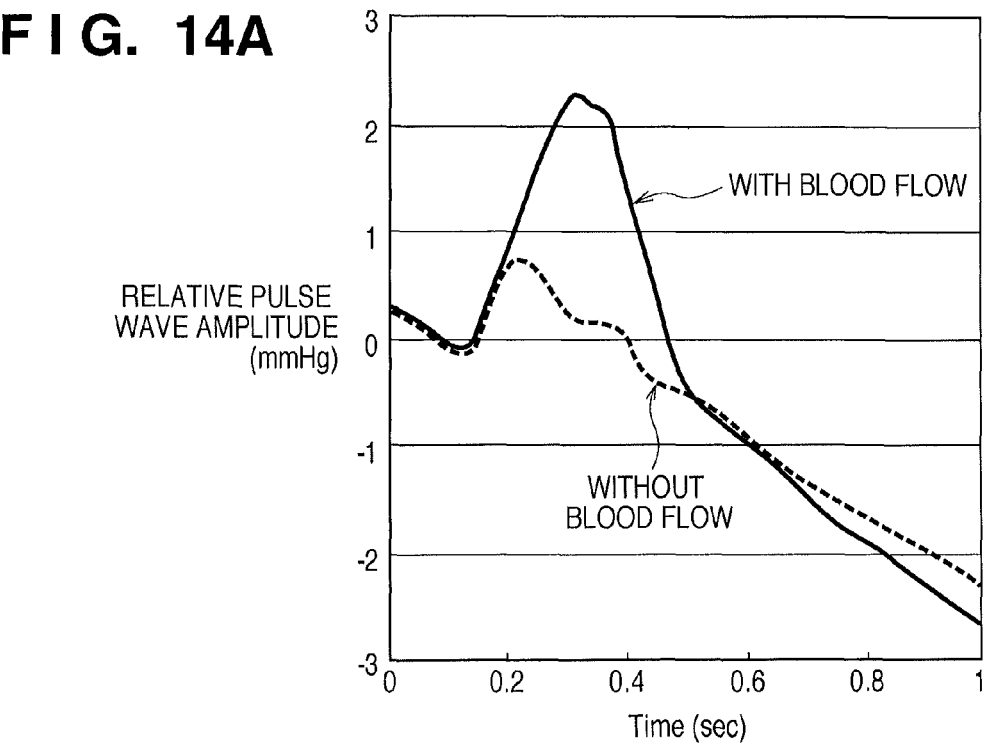
F I G. 14A
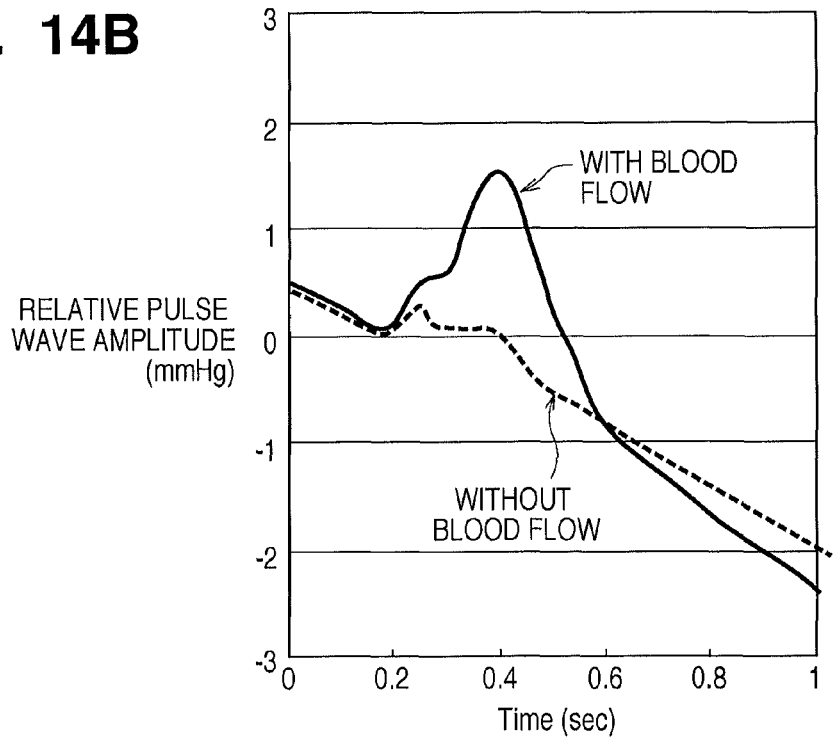
F I G. 14B

BLOOD PRESSURE MEASUREMENT DEVICE AND CONTROL METHOD OF THE SAME

TECHNICAL FIELD

The present invention relates to a blood pressure measurement technique and, more particularly, to the provision of information concerning the reliability of data used in the derivation of a blood pressure value.

BACKGROUND ART

Blood pressure measurement is very important in antihypertensive therapies. According to the guidelines for antihypertensive therapies of WHO/ISH, the degrees of hypertension are classified in accordance with blood pressure values measured every 5 mmHg, and therapeutic methods suitable for the individual degrees are recommended. Therefore, whether appropriate therapies can be performed depends on the measured blood pressure values. Also, as the aging of population advances in recent years, demands for high accuracy and high reliability of blood pressure measurement are greatly increasing in order to prevent circulatory organ diseases and metabolic syndrome on which hypertension has large effects.

Conventionally, measurement methods used for a non-invasive sphygmomanometer for measuring the blood pressure include winding a cuff around a blood pressure measurement portion, and gradually changing the cuff pressure from a pressure higher than the systolic blood pressure (also called a maximum blood pressure) to a pressure lower than the diastolic blood pressure (also called a minimum blood pressure), a microphone method that measures the blood pressure by detecting the Korotkoff sounds as in an auditory method and an oscillometric method that measures the blood pressure by detecting the change in pulse wave superposed on the internal pressure of an internal air bag of a cuff.

In addition, PLT1 has disclosed a double cuff method that further increases the measurement accuracy of the oscillometric method by setting a pulse wave detection cuff in a position slightly shifted toward the periphery from the center of a blood flow blocking air bag. Also, PLT2 has disclosed a technique that displays a two-dimensional graph having a first axis on which the pressing force of a cuff is a variant and a second axis on which the amplitude of a cuff pulse wave is a variant, in order to determine the reliability of a measured blood pressure value.
PLT1: Japanese Patent Laid-Open No. 2000-79101
PLT2: Japanese Patent Publication No. 2-25610

SUMMARY OF INVENTION

Technical Problem

The Korotkoff sound detection sensitivity of the microphone method and a practical blood pressure value deriving method in the oscillometric method described above vary from one sphygmomanometer manufacturer to another, and are not open to the public. For validating the accuracy of the measured systolic blood pressure value and diastolic blood pressure value, only the results of a few examples are announced based on the guidelines for comparison with the accuracy of the auditory method formed in EC or U.S.A.; the measurement accuracy of each individual measured and displayed blood pressure value and the basis on which the systolic blood pressure and diastolic blood pressure are determined are generally not disclosed.

The microphone method obtains the change in Korotkoff sounds, and the oscillometric method obtains the correlation between the change in pulse wave and the systolic blood pressure point and diastolic blood pressure point obtained by the auditory method, by statistical processing from a certain population, thereby measuring the blood pressure. Accordingly, these methods do not take into account the individual bodies and physiological variations of persons to be measured. Therefore, if a pulse wave amplitude change profile deviates from a general statistical distribution due to the difference between blood vessel extensibilities of individual persons or the existence of arrhythmia, it is sometimes impossible to derive a correct blood pressure value.

For example, the user cannot confirm whether each individual measurement value (blood pressure value) derived by a blood pressure measurement device is reliable. If a large artifact (noise caused by body motion) is mixed in, the use of the technique described in the afore-mentioned PLT2 makes it possible to determine whether the artifact has an effect on the accuracy. However, if a small artifact is mixed in, for example, if the respiration of a person to be measured fluctuates the cuff pulse wave, a satisfactory determination cannot be performed. Also, when the blood pressure value determination method itself is not open to the public, the user cannot determine what degree of noise has what kind of effect on the blood pressure value. If the measurement value is questionable, it is necessary to perform blood pressure measurement multiple times or to perform measurement by using the auditory method by a doctor, in order to perform more accurate measurement.

The present invention has been made in consideration of the above problems, and has as its object to provide a user with information by which the reliability of each individual derived measurement value can be determined.

Solution to Problem

To solve the above problems, a blood pressure measurement device according to the present invention has the following arrangement. That is, the blood pressure measurement device is characterized by comprising a cuff configured to press a blood pressure measurement portion, pressure control means for pressurizing or depressurizing an interior of the cuff, a pressure sensor which senses an internal pressure of the cuff, pulse wave signal extracting means for extracting time-series data of a pulse wave signal superposed on the cuff internal pressure sensed by the pressure sensor, in a process in which the pressure control means pressurizes or depressurizes the cuff, and display means for displaying a pulse waveform corresponding to a pulse wave signal of at least one period, together with a value of a cuff internal pressure corresponding to the pulse wave signal, based on the extracted pulse wave signal time-series data.

To solve the above problems, a control method of a blood pressure measurement device of the present invention has the following arrangement. That is, the control method of a blood pressure measurement device including a cuff configured to press a blood pressure measurement portion, pressure control means for pressurizing or depressurizing an interior of the cuff, and a pressure sensor which senses an internal pressure of the cuff, is characterized by comprising a pulse wave signal extracting step of extracting time-series data of a pulse wave signal superposed on a cuff internal pressure sensed by the pressure sensor, while the pressure control means is pressurizing or depressurizing the cuff, and a display step of displaying a pulse waveform corresponding to a pulse wave signal of at least one period, together with a value of a cuff internal pressure corresponding to the pulse wave signal, based on the extracted pulse wave signal time-series data.

Advantageous Effects of Invention

The present invention can provide a user with information by which the reliability of each individual measurement value derived by a blood pressure measurement device can be determined.

Other features and advantages of the present invention will be apparent from the following explanation taken in conjunction with the accompanying drawings. Note that the same reference numerals denote the same parts or similar parts in the accompanying drawings.

BRIEF DESCRIPTION OF DRAWINGS

The accompanying drawings, which are incorporated in and constitute a part of the specification, illustrate embodiments of the invention and, together with the description, serve to explain the principles of the invention.

FIG. 11A is a view showing an example of a graph displayed on an LCD;

FIG. 11B is a view showing the example of the graph displayed on the LCD;

FIG. 14A is a view showing a pulse wave signal of one period obtained by a double cuff; and FIG. 14B is a view showing a pulse wave signal of one period obtained by a triple cuff.

BEST MODE FOR CARRYING OUT THE INVENTION

First Embodiment

Preferred embodiments of a blood pressure measurement device according to the present invention will be explained below with reference to the accompanying drawings. In the following description, a pulse wave signal obtained by the oscillometric method in a cuff depressurizing process will be explained in detail first, and then details of the operation of the blood pressure measurement device of the present invention will be explained.

<Device Configuration>

Figure 8:
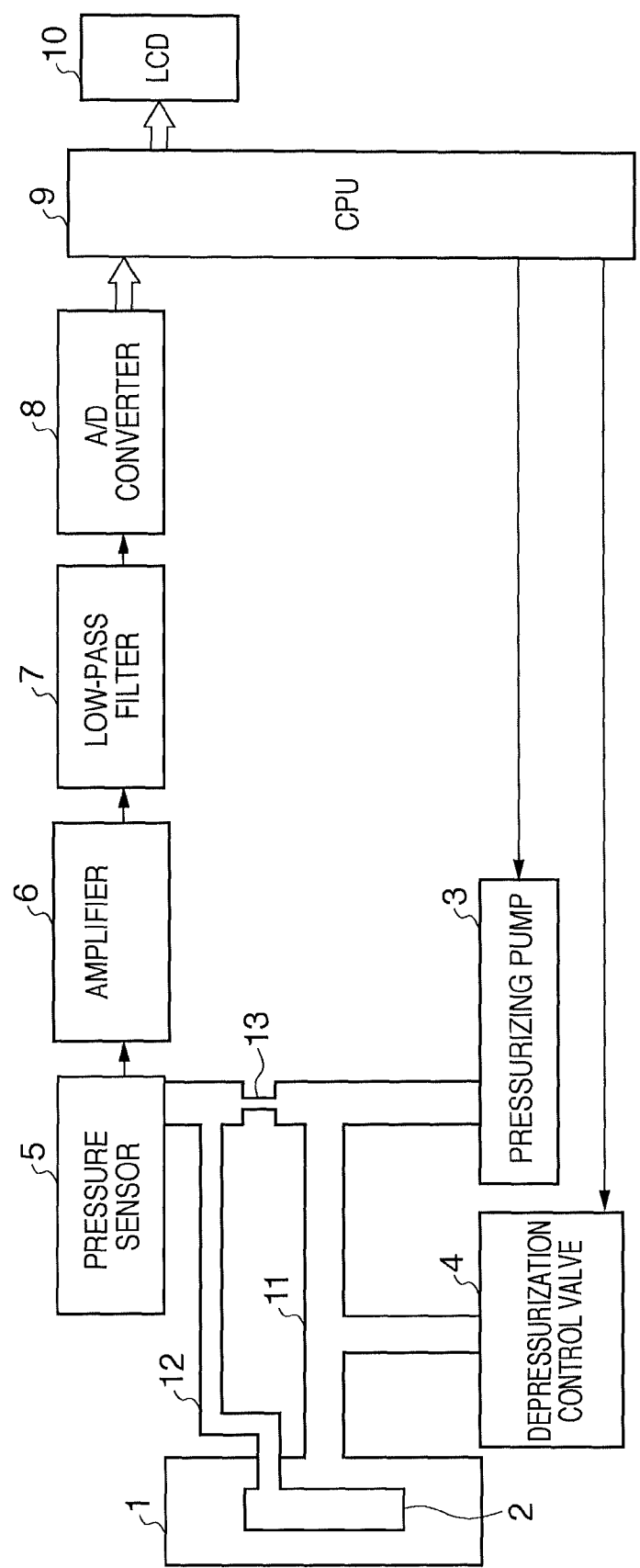
FIG. 8 is a view showing the arrangement of the blood pressure measurement device according to the first embodiment.

FIG. 8 is a view showing the arrangement of the blood pressure measurement device according to the first embodiment.

A large cuff 1 for blocking a blood vessel is connected to a pressurizing pump 3 and depressurization control valve (solenoid valve) 4 via a tube 11. The large cuff 1 is also connected to a pressure sensor 5 via a fluid resistance 13. A small cuff 2 for detecting a pulse wave is positioned in almost the center of the large cuff 1, and connected to the pressure sensor 5 via a tube 12. An outline of blood pressure measurement using this double cuff is disclosed in PLT1, as described in the BACKGROUND ART section.

The small cuff 2 for detecting a pulse wave is formed in a cuff central portion of the large cuff 1 for blocking a blood vessel, and best detects a blood vessel internal volume change in the cuff central portion. Also, the small cuff 2 is made as small as possible in order to reduce the attenuation of a pulse wave signal caused by the diffusion of pulse wave oscillation. The fluid resistance 13 is a mechanical filter for attenuating or interrupting a pulse wave signal to be detected by the large cuff 1. This enables the small cuff 2 to accurately detect the blood vessel internal volume change below the cuff. The pressure sensor 5 is, for example, a diaphragm type pressure-electricity converter using a semiconductor pressure gauge. An output signal (pressure signal) from the pressure sensor 5 is amplified by an amplifier 6, and converted into a digital signal by an A/D converter 8 via a low-pass filter 7, and this digital signal is input to a CPU 9. The low-pass filter 7 limits the frequency band of the output signal, thereby cutting off unnecessary high-frequency noise such as valve control noise. The cutoff frequency is set at 10 to 30 Hz.

The CPU 9 controls the pressurizing pump 3 and depressurization control valve (solenoid valve) 4. In particular, the opening/closing of the depressurization control valve (solenoid valve) 4 is controlled (by PWM control) by a PWM signal (ON/OFF pulse signal) from the CPU 9. The orifice area is continuously controlled by changing the duty of the PWM signal from complete "close" to complete "open".

Furthermore, the CPU 9 has a function of periodically receiving the digital pressure signal (cuff pressure signal) from the A/D converter 8, separating a pulse wave signal superposed on the cuff pressure signal, and determining the systolic blood pressure value and diastolic blood pressure value from the pulse wave signal and cuff pressure (signal). Note that details of the determination of the systolic blood pressure value and diastolic blood pressure value will be described later.

Also, the CPU 9 displays the thus determined systolic blood pressure value and diastolic blood pressure value on an LCD 10. In addition, the CPU 9 has a function of displaying a two-dimensional graph on the LCD 10. Therefore, the LCD 10 is, for example, a dot matrix LCD capable of displaying a two-dimensional graph.

<Cuff Pressing Force and Pulse Wave Signal>

Figure 1:
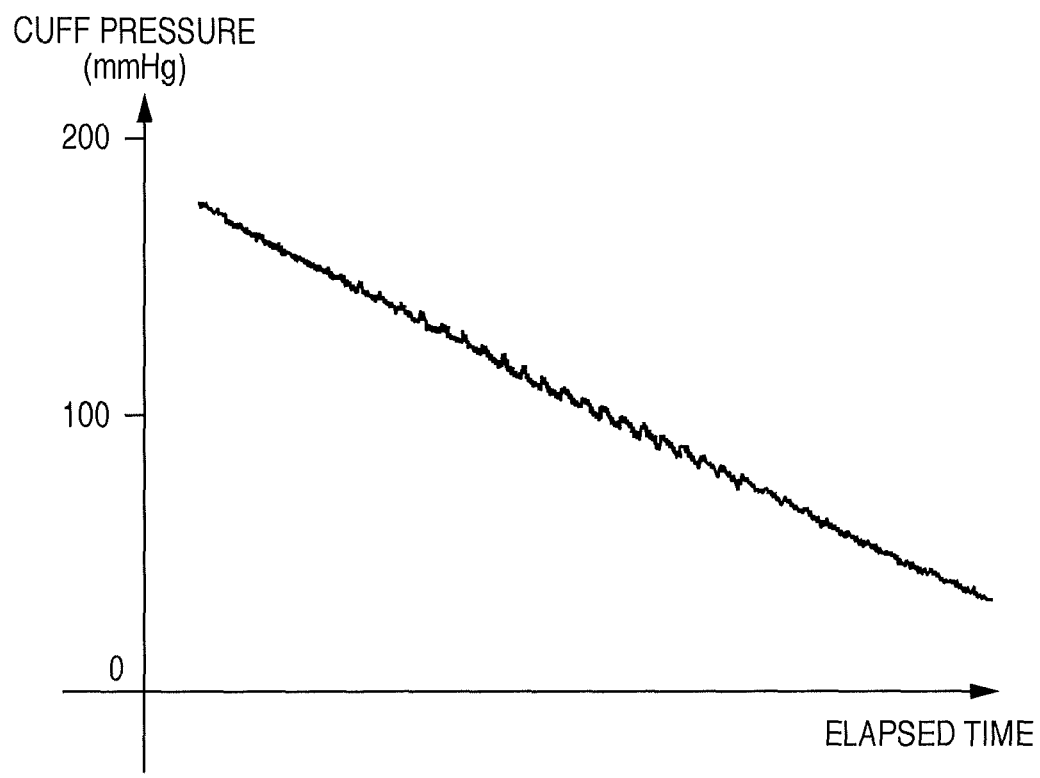
FIG. 1 is a view showing the way a pulse wave signal is superposed on the cuff pressure in a cuff depressurizing process.
Figure 2:
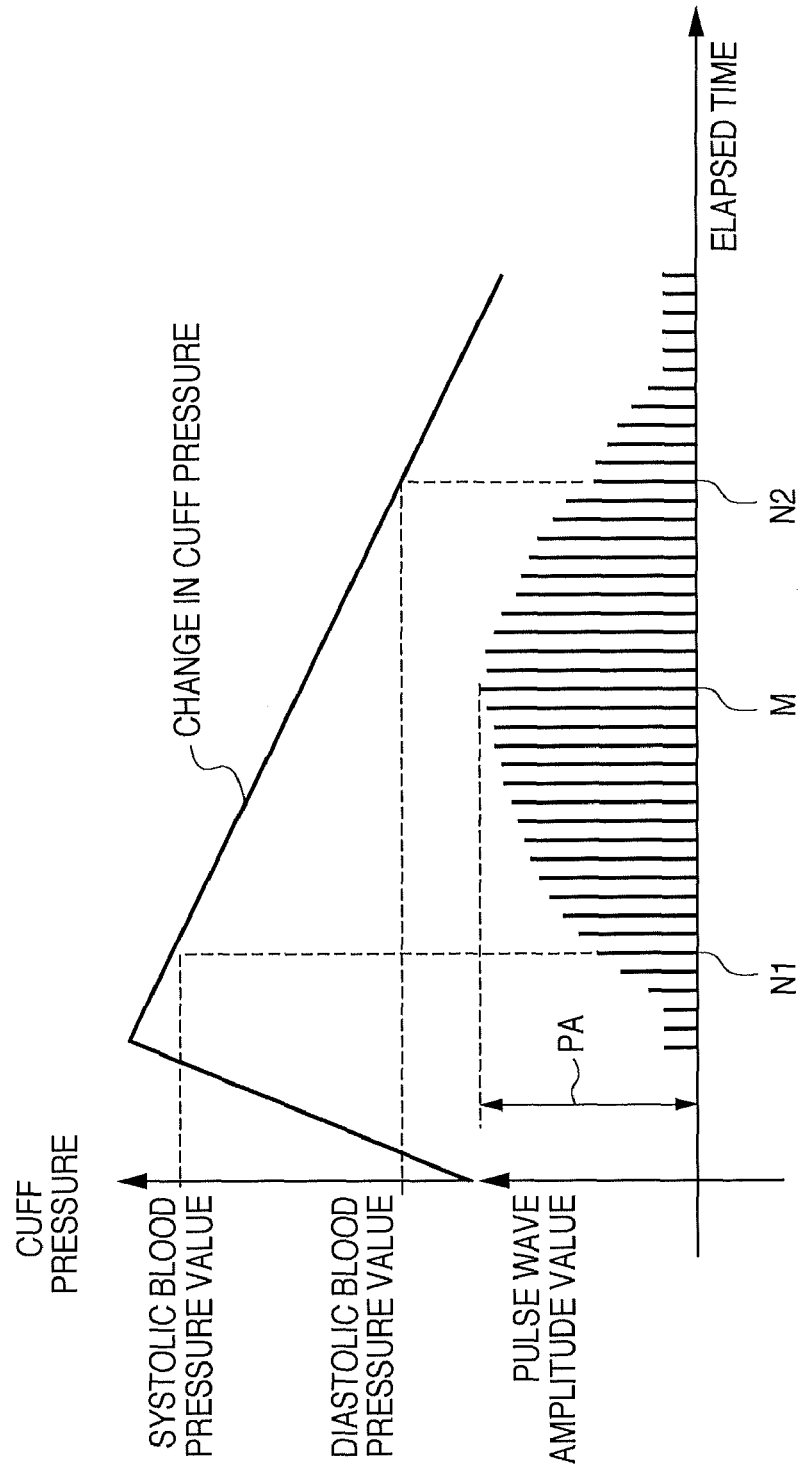
FIG. 2 is a view showing the way a pulse wave amplitude value superposed on the cuff pressure changes in the cuff depressurizing process, together with the change in cuff pressure.

FIG. 1 is a graph showing the way a pulse wave signal is superposed on the cuff pressure in a cuff depressurizing process. This graph shows the way the magnitude and shape of the pulse wave signal change as the cuff pressure reduces. FIG. 2 is a view showing the way a pulse wave amplitude value to be superposed on the cuff pressure changes in the cuff depressurizing process, together with the change in cuff pressure. FIG. 2 shows that in the cuff depressurizing process, the pulse wave amplitude value first gradually increases and then gradually decreases after a point M at which a maximum amplitude value appears.

Figure 3:
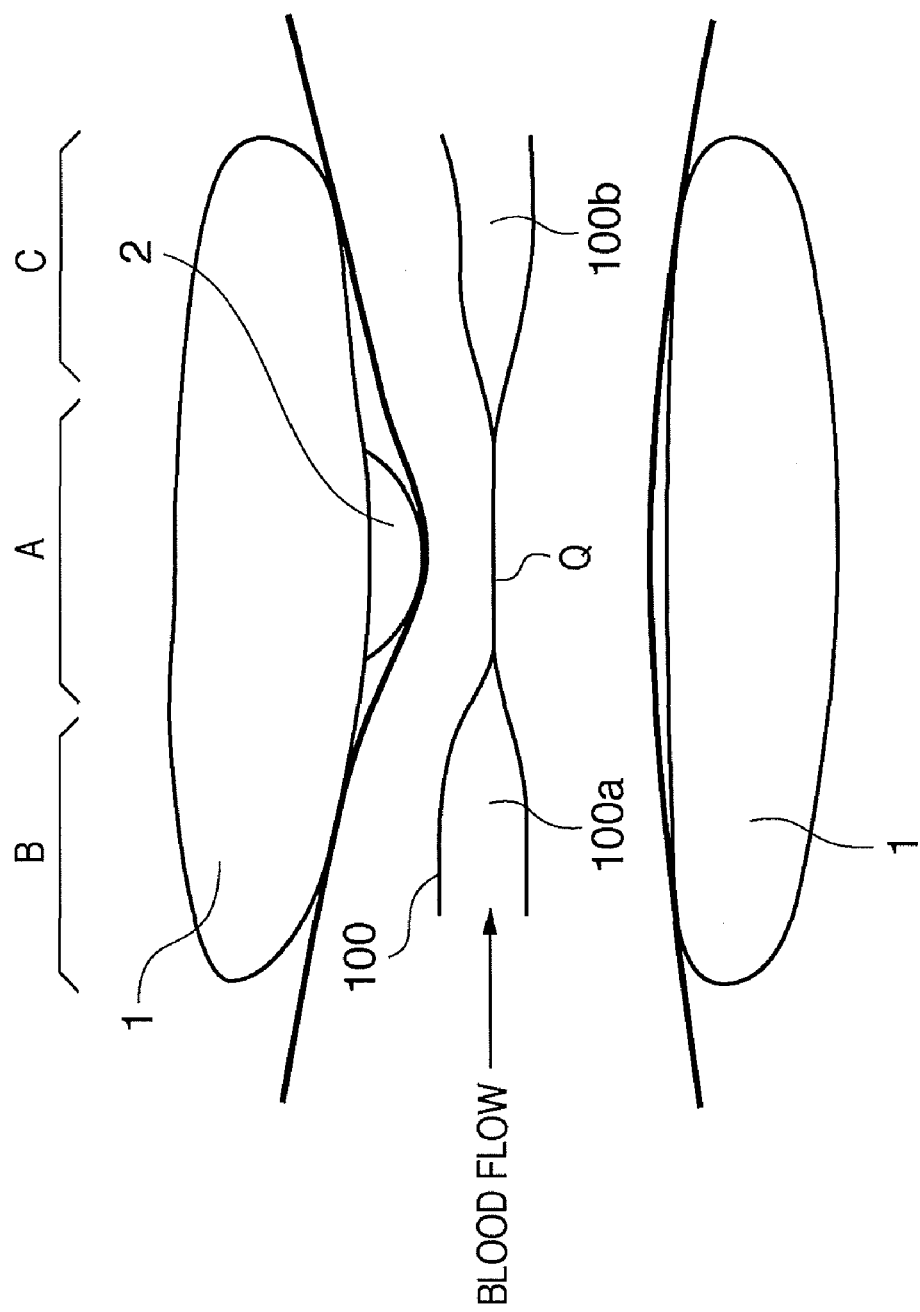
FIG. 3 is a sectional view in the longitudinal direction of a cuff (double cuff) of a blood pressure measurement device according to the first embodiment.

FIG. 3 is a sectional view in the longitudinal direction (in which the upper arm extends) of the cuff (double cuff) of the blood pressure measurement device according to the first embodiment. As described above, the cuff according to the first embodiment is a double cuff including the large cuff (first cuff) 1 for blocking a blood vessel and the small cuff (second cuff) 2 for detecting a pulse wave. FIG. 3 shows the way the pressurized large cuff 1 for blocking a blood vessel blocks a portion Q of a blood vessel 100, thereby suppressing a blood flow from an upstream side 100a to a downstream side 100b.

The force with which the large cuff 1 presses the arm is strongest in a central portion (a portion A in FIG. 3; to be simply referred to as a cuff central portion A hereinafter) in the cuff widthwise direction. The pressing force weakens toward the two ends, and is almost 0 at the two ends. The small cuff 2 is formed in the cuff central portion A in the cuff widthwise direction, and hence best detects a blood vessel internal pressure change (blood vessel internal volume change) in this portion. Note that "the cuff pressure" means the internal pressure of the cuff in this specification. In practice, however, the cuff pressure is equal to the arm pressing force in the cuff central portion A in the cuff widthwise direction. Therefore, the cuff pressure is also the pressure applied from the cuff to the blood vessel below the cuff central portion A in the cuff widthwise direction.

<Properties of Components Forming Pulse Wave Signal>

A pulse wave signal to be superposed on the cuff pressure, which is detected by the small cuff 2 for detecting a pulse wave, is divided into a component W1 (to be referred to as a W1 component hereinafter) resulting from a direct pressure change (blood vessel internal volume change) caused by a blood flow output from the upstream side of the cuff, and a component W2 (to be referred to as a W2 component hereinafter) resulting from a pressure change (blood vessel internal volume change) caused by the reflection from a blood vessel downstream of the cuff. The W1 component can be divided into a component W1-A (to be referred to as a W1-A component hereinafter) resulting from a pressure change (blood vessel internal volume change) below the central portion of the cuff widthwise direction, that is, the cuff central portion A, a component W1-B (to be referred to as a W1-B component hereinafter) resulting from a pressure change (blood vessel internal volume change) below an upstream portion in the cuff widthwise direction, that is, a portion B (to be simply referred to as a cuff upstream portion B hereinafter) shown in FIG. 3, and a component W1-C (to be referred to as a W1-C component hereinafter) resulting from a blood vessel internal volume change below a downstream portion in the cuff widthwise direction, that is, a portion C (to be simply referred to as a cuff downstream portion C hereinafter) shown in FIG. 3.

Figure 5:
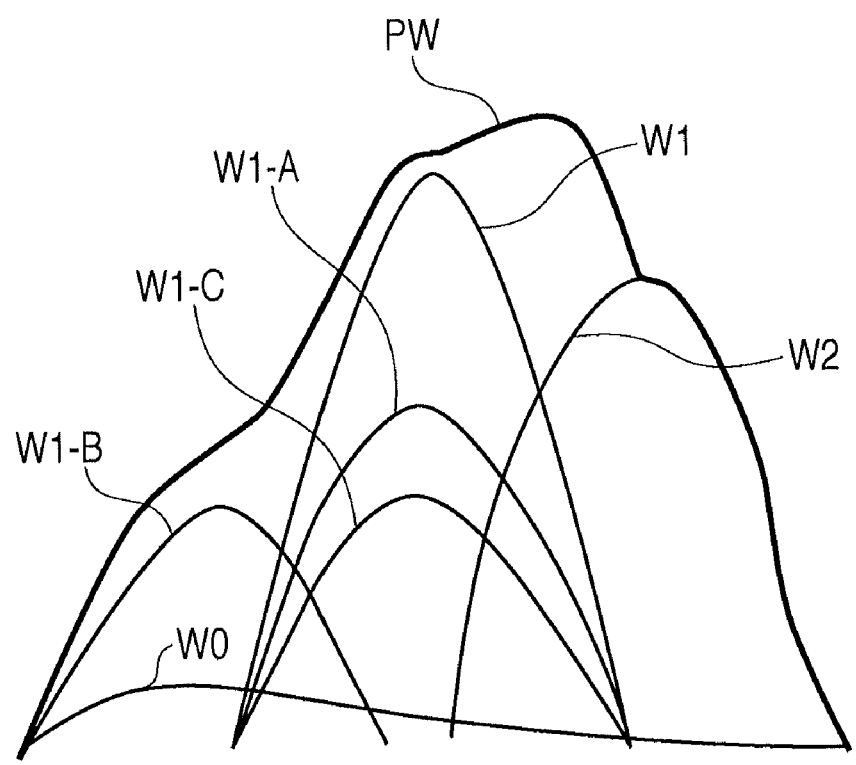
FIG. 5 is an exemplary view showing components contained in a pulse wave signal PW (in a double cuff)

FIG. 5 is an exemplary view showing the components contained in a pulse wave signal PW. More specifically, the pulse wave signal PW indicated by the thick line contains the W1 and W2 components, and the W1 component further contains the W1-A, W1-B, and W1-C components.

The pulse wave signal PW is a typical example observed when the cuff pressure is between the systolic blood pressure value and diastolic blood pressure value in the depressurizing process. When the cuff pressure is between the systolic blood pressure value and diastolic blood pressure value in the depressurizing process, a phenomenon in which the blood flows into the cuff central portion A and outputs a blood flow to the blood vessel downstream of the cuff is observed. In this case, the W1-A component resulting from the blood vessel internal volume change below the cuff central portion A caused by the blood flow output to the blood vessel on the downstream side and the W1-C component resulting from the blood vessel internal volume change below the cuff downstream portion C overlap, with a time delay, that is, a time difference, the W1-B component resulting from the blood vessel internal volume change caused by the blood flowing below the cuff upstream portion B, thereby forming the W1 component. In addition, the W2 component due to the reflection from the downstream side overlaps the W1 component with a time difference, thereby forming the pulse wave signal PW superposed on the cuff pressure.

The small cuff 2 for detecting a pulse wave is attached to almost the cuff central portion A, and hence best detects the W1-A component compared to the W1-B and W1-C components. Accordingly, the feature of the W1-A component is largely reflected on the shape of the W1 component, compared to the features of the W1-B and W1-C components.

The W1-B component indicates the blood vessel internal volume change below the cuff upstream portion B. Since the upstream portion B is positioned on the upstream side (heart side) compared to the central portion A and downstream portion C, the W1-B component appears earlier than the W1-A and W1-C components, and is reflected on the shape of the leading edge of the W1 component. The W1-C component indicates the blood vessel internal volume change below the cuff downstream portion C. Since the downstream portion C is positioned downstream of the central portion A and the cuff pressing force in the downstream portion C is smaller than that in the central portion A, the opening/closing of the blood vessel below the downstream portion C is almost synchronized with that of the blood vessel below the central portion A, and there is practically no time difference between the appearances of the W1-A and W1-C components.

The W2 component is the reflection from the blood vessel downstream of the cuff with respect to the blood flow output from the upstream side. Therefore, the peak appears later or earlier than that of the W1 component in accordance with the timing at which the blood vessel internal pressure on the downstream side becomes higher than the cuff pressure. FIG. 5 shows the state in which the peak of the W2 component appears later than that of the W1 component. The reflection of the shape of the W2 component on the overall shape of the pulse wave signal is generally smaller than that of the shape of the W1 component (the synthesis of the W1-A, W1-B, and W1-C components). Also, when the cuff pressure is close to the diastolic blood pressure value in the depressurizing process, the blood vessel internal pressure on the cuff downstream side has well recovered to the state before the blood flow is blocked by the cuff, so there is practically no reflection from the blood vessel on the downstream side. Accordingly, the W2 component has practically disappeared from a pulse wave signal detected when the cuff pressure is close to the diastolic blood pressure value.

Figure 6:
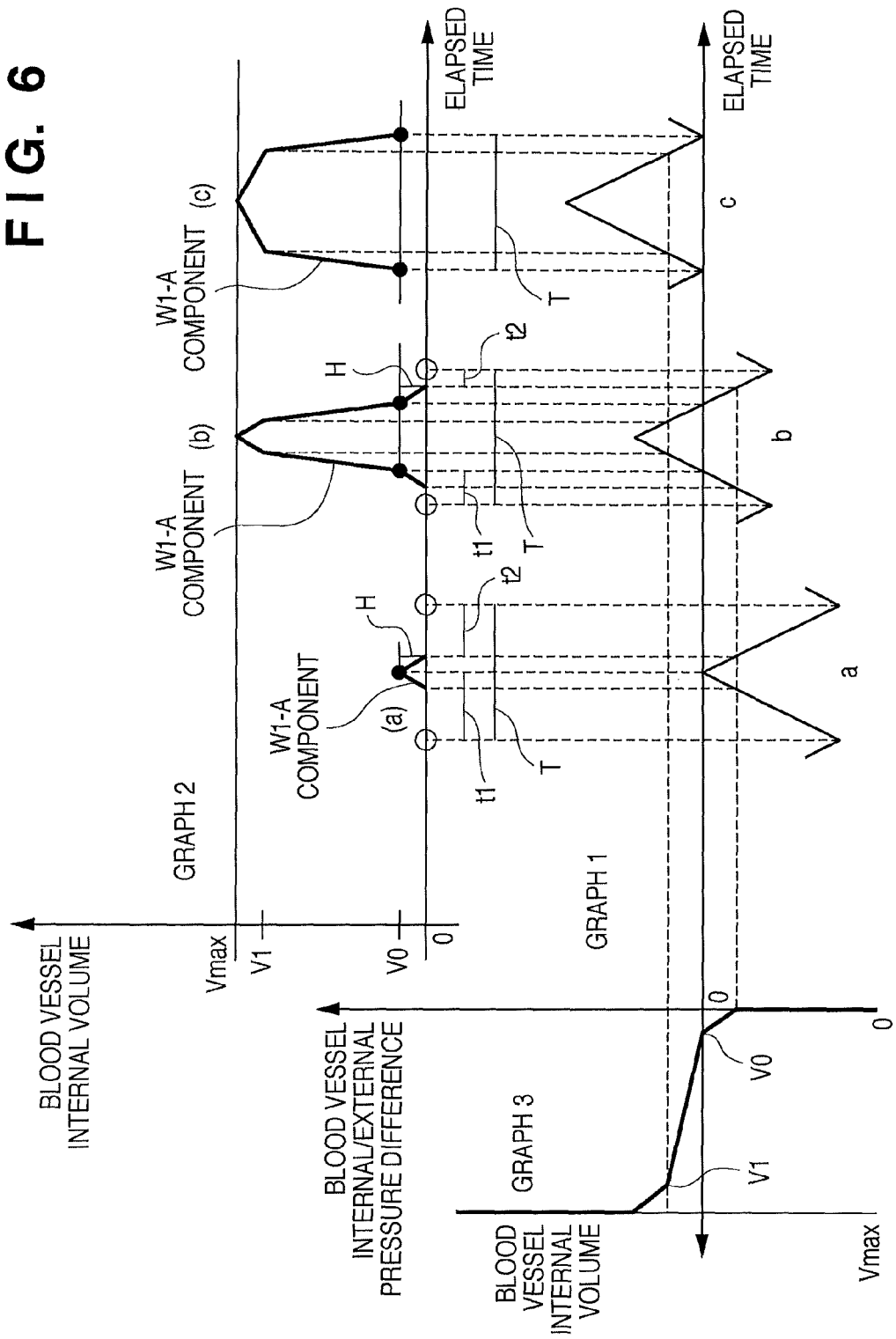
FIG. 6 is an exemplary view showing the way a W1-A component resulting from a blood vessel internal volume change below a cuff central portion A forms and changes in the cuff depressurizing process.

FIG. 6 is an exemplary view showing the way the W1-A component resulting from the blood vessel internal volume change below the cuff central portion A forms and changes in the cuff depressurizing process.

In graph 1, the abscissa represents the elapsed time when the cuff pressure is reduced at a constant depressurization rate, the ordinate represents the blood vessel internal/external pressure difference (blood vessel internal pressure−cuff pressure), and the invasive waveform (blood vessel internal pressure change) is simplified by a triangular waveform. Based on these conditions, graph 1 represents the change (the same triangular waveform as the invasive waveform) in blood vessel internal/external pressure difference below the cuff central portion A, which results from the invasive waveform (blood vessel internal pressure change) at each point of the elapsed time.

Above graph 1, graph 2 represents the change in blood vessel internal volume at each point of time, which occurs in response to the change in blood vessel internal/external pressure difference, by plotting the blood vessel internal volume on the ordinate. On the left side of the ordinate of the blood vessel internal/external pressure difference, graph 3 represents a blood vessel internal/external pressure difference-blood vessel internal volume relationship that converts the blood vessel internal/external pressure difference change (graph 1) into the blood vessel internal volume change (graph 2), by plotting the blood vessel internal volume on the abscissa.

As the blood vessel internal/external pressure difference-blood vessel internal volume relationship of graph 3, a simplified relationship is assumed by noting the tendency that the blood vessel internal volume abruptly changes (abruptly increases or decreases) near the position where the blood vessel internal/external pressure difference is 0. That is, a line including two bent portions at points where the blood vessel internal volume is V0 and V1, a steep gradient portion between V0 and V1, and gentle gradient portions smaller than V0 and larger than V1 represents the change between the state (the blood vessel internal volume is 0) in which the blood vessel is completely closed and the state (the blood vessel internal volume is Vmax) in which the blood vessel is completely open in the process during which the blood vessel internal/external pressure difference increases and decreases.

This indicates two tendencies: one is the tendency that the blood vessel is collapsed by its own weight (the blood vessel internal volume is V0) in a position where the blood vessel internal/external pressure difference is 0, but the blood vessel internal volume abruptly increases to reach the state in which the blood vessel is well open (the blood vessel internal volume is V1) when the blood vessel internal/external pressure difference changes from the above-mentioned position to a positive value, and the blood vessel internal volume gradually increases (toward the maximum blood vessel internal volume Vmax) with respect to the change in blood vessel internal/external pressure difference; and the other is the tendency that when the blood vessel internal/external pressure difference changes from the position where it is 0 to a negative value, the blood vessel internal volume gradually decreases (toward a blood vessel internal volume of 0). Note that in graph 3, the steep gradient portion between the positions where the blood vessel internal volume is V0 and V1 is approximated by a straight line, so the ratio of the change in blood vessel internal volume remains the same in this portion. In practice, however, the ratio of the change is maximum at the position where the blood vessel internal/external pressure difference is 0 (the position where the blood vessel internal volume is V0).

The degree of the tendency that the blood vessel internal volume abruptly changes (abruptly increases) near the position where the blood vessel internal/external pressure difference is 0 depends on the extensibility of the blood vessel of a person to be measured. However, the tendency itself is presumably generalizable.

In the cuff depressurizing process (elapsed time) of graph 1, a, b, and c respectively indicate the change (triangular wave) in blood vessel internal/external pressure difference below the cuff central portion A, when the cuff pressure is equal to the systolic blood pressure value, when the cuff pressure is in almost the middle of the systolic blood pressure value and diastolic blood pressure value, and when the cuff pressure is equal to the diastolic blood pressure.

The changes (triangular waveforms) a, b, and c in blood vessel internal/external pressure difference at the individual points of the elapsed time each have an apex (peak point) resulting from the portion of the systolic blood pressure value (i.e., the initial diastolic period of the heart) in the invasive waveform (blood vessel internal pressure change), and a downward apex (bottom point) resulting from the portion of the diastolic blood pressure value (i.e., the initial systolic period of the heart) in the invasive waveform (blood vessel internal pressure change).

(a), (b), and (c) in graph 2 respectively indicate the results of the conversion of the changes in blood vessel internal/external pressure difference of a, b, and c in graph 1 into the changes in blood vessel internal volume by using the blood vessel internal/external pressure difference-blood vessel internal volume relationship in graph 3. In (a), (b), and (c), hollow circles indicate the positions (two, front and back portions) of the initial systolic period of the heart. Each hollow circle corresponds to the downward apex (bottom point) of the invasive waveform (blood vessel internal pressure change). A component (indicated by the thick line) shown between the positions (two, front and back portions) of the initial systolic period of the heart is the W1-A component. That is, graph 2 shows the way the W1-A component changes at each point of time in the cuff depressurizing process (elapsed time).

In the W1-A components (blood vessel internal volume changes) of (b) and (c), each dot indicates the position where the blood vessel internal/external pressure difference is 0 before the peak point. In the W1-A component (blood vessel internal volume change) of (a), the peak point corresponds to the position where the blood vessel internal/external pressure difference is 0, and a dot indicates this position. The position where the blood vessel internal/external pressure difference is 0 indicated by the dot in each of (a), (b), and (c) is actually a portion (a maximum gradient point in the first half of the waveform) where the blood vessel internal volume abruptly increases (abruptly rises).

In addition, in the W1-A components of (a), (b), and (c), a position where the blood vessel internal volume is minimum, which is produced after the peak point, is also indicated by a dot. This position where the blood vessel internal volume is minimum, which is produced after the peak point of the W1-A component, is almost equal to the position of the downward peak point (bottom point) of an actual pulse wave signal. Accordingly, the position where the blood vessel internal volume is minimum, which is produced after the peak point of the W1-A component, will be called a bottom point of the W1-A component.

In graph 2, t1 indicates a time (time difference) by which the portion (the maximum gradient point in the first half of the waveform) where the blood vessel internal volume abruptly rises in the W1-A component [the position indicated by the dot where the blood vessel internal/external pressure difference is 0] lags behind the position of the initial systolic period leading the W1-A component, t2 indicates a time (time difference) by which the bottom point of the W1-A component leads the position of the next initial systolic period, and T indicates one period of the pulse wave signal. The period T of the pulse wave signal is practically constant during the measurement period. Also, H indicates the displacement of the bottom point of the W1-A component below the portion (the maximum gradient point in the first half of the waveform) where the blood vessel internal volume abruptly rises.

Let t be the sum of the lagging time (time difference) t1 and the leading time (time difference) t2 (t=t1+t2). Since t1 and t2 are almost equal in a continuously produced W1-A component, t presumably indicates the time (time difference) by which the portion (the maximum gradient point in the first half) where a W1-A component of interest lags behind the bottom point of the preceding W1-A component, that is, the time difference between the preceding bottom point (of the W1-A component) and the appearance of the maximum gradient point.

As indicated by (a), (b), and (c) in graph 2, the time difference t1 and time difference t2 decrease as the cuff pressure approaches the diastolic blood pressure value from the systolic blood pressure value. That is, the time difference t between the preceding bottom point and the appearance of the maximum gradient point decreases as the cuff pressure approaches the diastolic blood pressure value from the systolic blood pressure value. Since the period T of the pulse wave signal is practically constant during the measurement period, a phase difference 2π (t/T) between the preceding bottom point and the appearance of the maximum gradient point similarly decreases as the cuff pressure approaches the diastolic blood pressure value from the systolic blood pressure value.

As indicated by (c) in graph 2, when the cuff pressure is equal to the diastolic blood pressure value, the preceding bottom point and maximum gradient point (abrupt rising point) of the W1-A component and the initial systolic period occur at the same time, that is, t1=0, t2=0, and t=0, in this simplified graph.

In addition, (b) and (c) in graph 2 reveal that the downward displacement H of the bottom point of the W1-A component from the maximum gradient point (abrupt rising point) decreases as the cuff pressure approaches the diastolic blood pressure value. As indicated by (c), when the cuff pressure is equal to the diastolic blood pressure value, the positions of the bottom point and maximum gradient point of the W1-A component match, that is, H=0 (the displacement disappears), in this simplified graph.

From the foregoing, the actual W1-A component has the following three features.

The delay (the time difference t or the phase difference 2π (t/T)) of the steep rising portion (maximum gradient point) of the W1-A component from the bottom point decreases as the cuff pressure approaches the diastolic blood pressure value.

The displacement H of the bottom point from the steep rising portion (maximum gradient point) of the W1-A component decreases as the cuff pressure approaches the diastolic blood pressure value.

The shape of the W1-A component appears when the cuff pressure becomes lower than the pressure of the systolic blood pressure value.

<Features of Pulse Wave Signal>

The contents of the simplified examination of the W1-A component obtained by dividing the pulse wave signal PW into components have been described above. In practice, however, the small cuff 2 for detecting a pulse wave detects the pulse wave signal PW as one pulse wave signal on which the W1-A and W1-B components are superposed, without separating the pulse wave signal PW into these components.

As described previously, however, although the W1-B component is reflected on the leading edge of the W1 component, the W1-A component largely reflects the shape of the W1 component of the pulse wave signal to be superposed on the cuff pressure. In addition, the W2 component of the pulse wave signal is generally smaller than the W1 component, and disappears when the cuff pressure is close to the diastolic blood pressure value.

Accordingly, the pulse wave signal to be detected has the following three features.

The delay (the time difference t or the phase difference 2π (t/T)) of the steep rising portion (maximum gradient point) of the pulse wave signal from the bottom point decreases as the cuff pressure approaches the diastolic blood pressure value.

The displacement H of the bottom point from the steep rising portion (maximum gradient point) of the pulse wave signal decreases as the cuff pressure approaches the diastolic blood pressure value.

The steep rising portion of the pulse wave signal largely changes when the cuff pressure becomes lower than the pressure of the systolic blood pressure value.

Figure 7A:
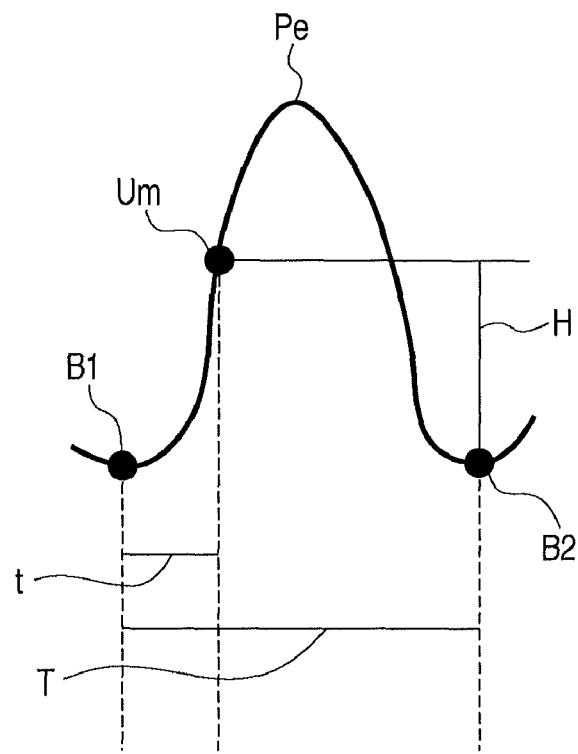
FIG. 7A is a view showing a pulse wave signal superposed on the cuff pressure detected when the cuff pressure is between a systolic blood pressure value and diastolic blood pressure value.
Figure 7B:
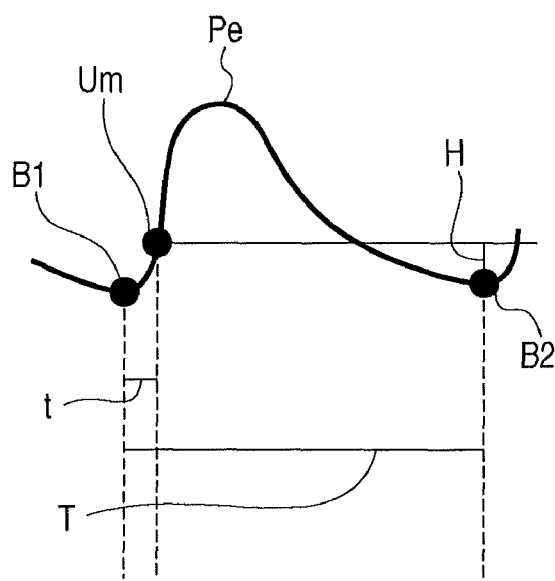
FIG. 7B is a view showing a pulse wave signal superposed on the cuff pressure detected when the cuff pressure is equal to the diastolic blood pressure value.

FIGS. 7A and 7B are views each showing the pulse wave signal superposed on the cuff pressure detected when the cuff pressure is between the systolic blood pressure value and diastolic blood pressure value, and when the cuff pressure is equal to the diastolic blood pressure value.

Each pulse wave signal has a steep rising portion (maximum gradient point) Um in the first half, a peak point Pe, and two bottom points B1 and B2 produced ahead of and behind the peak point Pe. FIGS. 7A and 7B also show the time difference t of the maximum gradient point Um from the bottom point B1, the period T, and the downward displacement H of the bottom point B2 from the maximum gradient point (abrupt rising point) Um. Note that the bottom point B1 is also the bottom point B2 produced behind the peak point of the preceding pulse wave signal, and successively produced pulse wave signals have almost the same shape. Therefore, the displacement of the bottom point B2 of a pulse wave signal of interest from the maximum gradient point (abrupt rising point) Um is almost the same as that of the bottom point B1 from the maximum gradient point (abrupt rising point) Um.

As described above, the time difference t (phase difference 2π (t/T)) and displacement H when the cuff pressure is equal to the diastolic blood pressure value are smaller than those when the cuff pressure is between the systolic blood pressure value and diastolic blood pressure value.

The W1-A component reflects the shape of the W1 component of the pulse wave signal to be superposed on the cuff pressure higher than the W1-B component. This means that when the W1-A component appears, the position where the steep rising portion (maximum gradient point) Um appears changes from the portion formed by reflecting the W1-B component to the position where the W1-A component appears. Since the W1-A component appears for the first time when the cuff pressure is less than or equal to the systolic blood pressure value, the shape of the steep rising portion (maximum gradient point) Um when a pressure higher than the systolic blood pressure value largely changes when the blood pressure value is less than or equal to the systolic blood pressure value.

<Determination of Blood Pressure Values>

Accordingly, the blood pressure values can be determined as follows based on the above-described features of the pulse wave signal.

The cuff pressure when the phase difference between the bottom point produced ahead of the peak point of the pulse wave signal and the appearance of the maximum gradient point (abrupt rising point) is smaller than a predetermined threshold value is set as the diastolic blood pressure value (diastolic blood pressure value determination 1).

The cuff pressure when the displacement (amplitude value difference) of the bottom point produced ahead of or behind the peak point of the pulse wave signal from the maximum gradient point (abrupt rising point) is smaller than a predetermined threshold value is set as the diastolic blood pressure value (diastolic blood pressure value determination 2).

The values of the cuff pressure when the phase difference between the bottom point produced ahead of the peak point of the pulse wave signal and the appearance of the maximum gradient point (abrupt rising point) are checked in order from a pulse wave signal corresponding to the lowest cuff pressure, and the cuff pressure value at a point showing a large change having no value continuity is set as the systolic blood pressure value (systolic blood pressure value determination 1).

The values of the displacement (amplitude value difference) of the bottom point produced ahead of or behind the peak point of the pulse wave signal from the maximum gradient point (abrupt rising point) are checked in order from a pulse wave signal corresponding to the lowest cuff pressure, and the cuff pressure value at a point showing a large change having no value continuity is set as the systolic blood pressure value (systolic blood pressure value determination 2).

As described above, the bottom point and maximum gradient point (abrupt rising point) of the pulse wave signal are detected in each individual pulse wave signal. Also, the predetermined threshold values are set by taking account of, for example, noise during the course of processing the detected pulse wave signal. Note that the effect of the individual difference or the measurement conditions such as the depressurization rate on, for example, noise in the course of the signal processing is generally small.

Unlike the conventional oscillometric sphygmomanometer, these blood pressure value determination methods need not handle the change profile of a pulse wave amplitude value in the cuff depressurizing process using parameters (e.g., the ratio of the pulse wave amplitude value to the maximum pulse wave amplitude value, which is set based on a statistical method) on which the individual difference of a person to be measured and the measurement conditions (e.g., the depressurization rate) have large effects. This makes it possible to perform measurement by reducing variations caused by the individual difference and the measurement conditions (e.g., the depressurization rate).

Note that data of the pulse wave signal must be acquired with high temporal resolution in order to identify the W1-A and W1-C components with high accuracy. To this end, the sampling rate of the A/D converter 8 is desirably, for example, 250 Hz or more. Note that the conventional oscillometric method uses a sampling rate of, for example, about 100 Hz because only the change in pulse wave amplitude need be measurable.

<Operation of Device>

Figure 9:
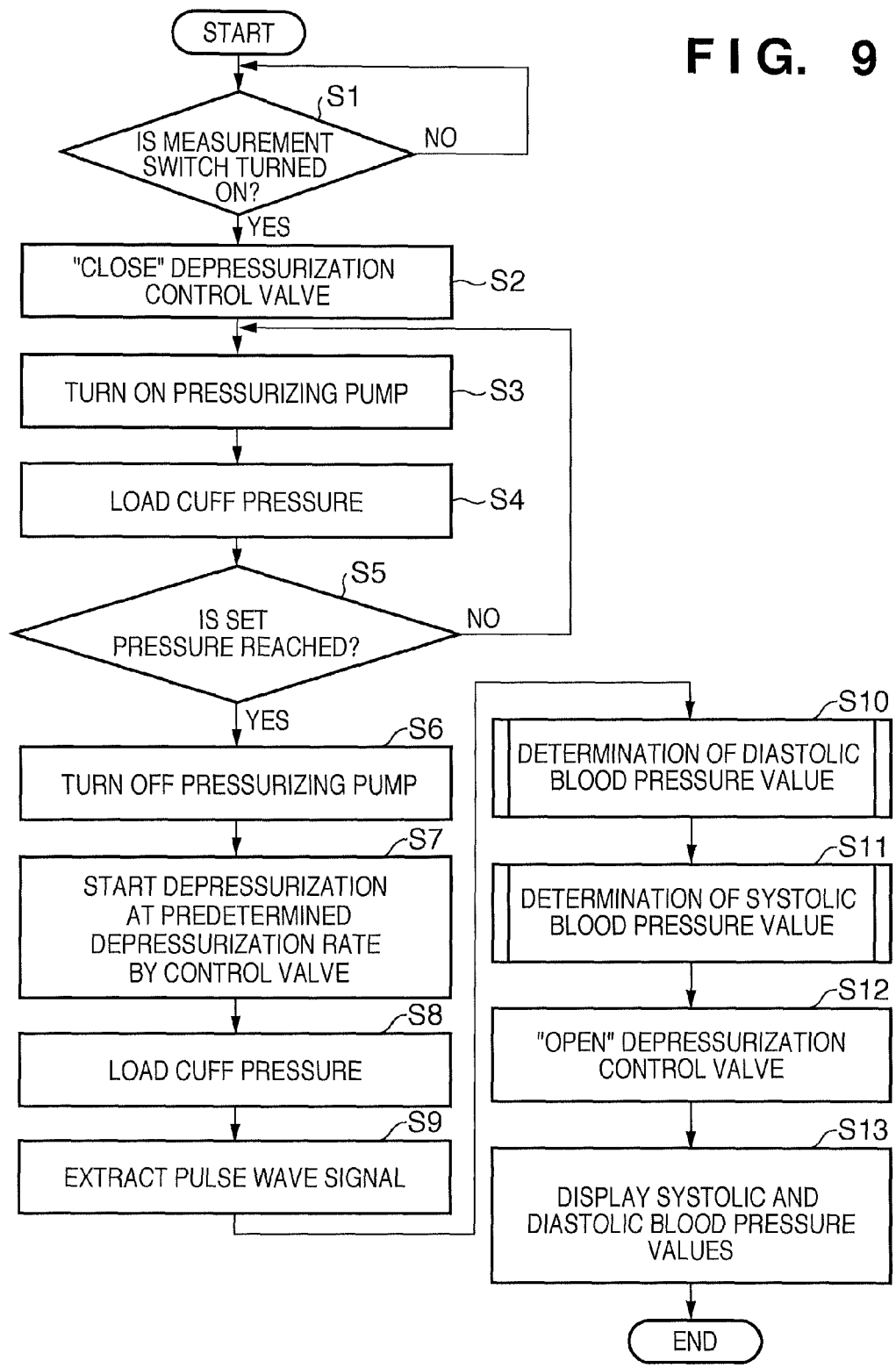
FIG. 9 is a flowchart showing an outline of the operation of the blood pressure measurement device according to the first embodiment.

FIG. 9 is a flowchart showing an outline of the operation of the blood pressure measurement device according to the first embodiment.

When a measurement start SW (switch) of the electronic sphygmomanometer is turned on (step S1), the depressurization control valve 4 is completely "closed" (step S2), and the driving of the pressurizing pump 3 is started (turned on) under the control of the CPU 9 (step S3).

When the pressurizing pump 3 is driven, the loading of the cuff pressure is started (step S4), and whether the loaded cuff pressure has a pressure value (set pressure) sufficiently higher than a preset systolic blood pressure value is determined (step S5). The pressurizing pump is kept driven until the cuff pressure reaches the set pressure. When the cuff pressure has reached the set pressure, the driving of the pressurizing pump 3 is stopped (turned off) (step S6).

After that, the CPU 9 controls the depressurization control valve 4 to start slow exhaust, thereby starting slow depressurization at a predetermined depressurization rate (e.g., 2 to 3 mmHg/sec) (step S7). In this depressurizing process, the CPU 9 loads the cuff pressure every predetermined time interval (every sampling time) (step S8), and extracts the pulse wave signal superposed on the cuff pressure (step S9). Note that when extracting the pulse wave signal, processing can be performed such that a direct-current (DC) offset corresponding to the cuff pressure is either included or excluded.

Based on the pulse wave signals extracted in step S9, the values of the pulse wave phase difference (t/T) are each derived every pulse wave period, in order from a pulse wave signal corresponding to the highest cuff pressure. A point at which the value of the phase difference is smaller than a predetermined threshold value is searched for, and the cuff pressure value corresponding to the detected point is determined as the diastolic blood pressure value (step S10). After that, a point at which the value of the phase difference largely changes is searched for in the acquired pulse wave signals from a pulse wave signal corresponding to the lowest cuff pressure, and the cuff pressure value corresponding to the detected point is determined as the systolic blood pressure value (step S11). Note that a flowchart for determining the systolic blood pressure value and diastolic blood pressure value will be described later.

After each blood pressure value is determined, the cuff pressure is returned to the atmospheric pressure by fully opening (completely "opening") the depressurization control valve (step S12). Then, the LCD 10 displays the stored systolic blood pressure value and diastolic blood pressure value under the control of the CPU 9 (step S13). Note that the LCD 10 also displays a graph as the basis of the blood pressure determination as will be described later.

Figure 10:
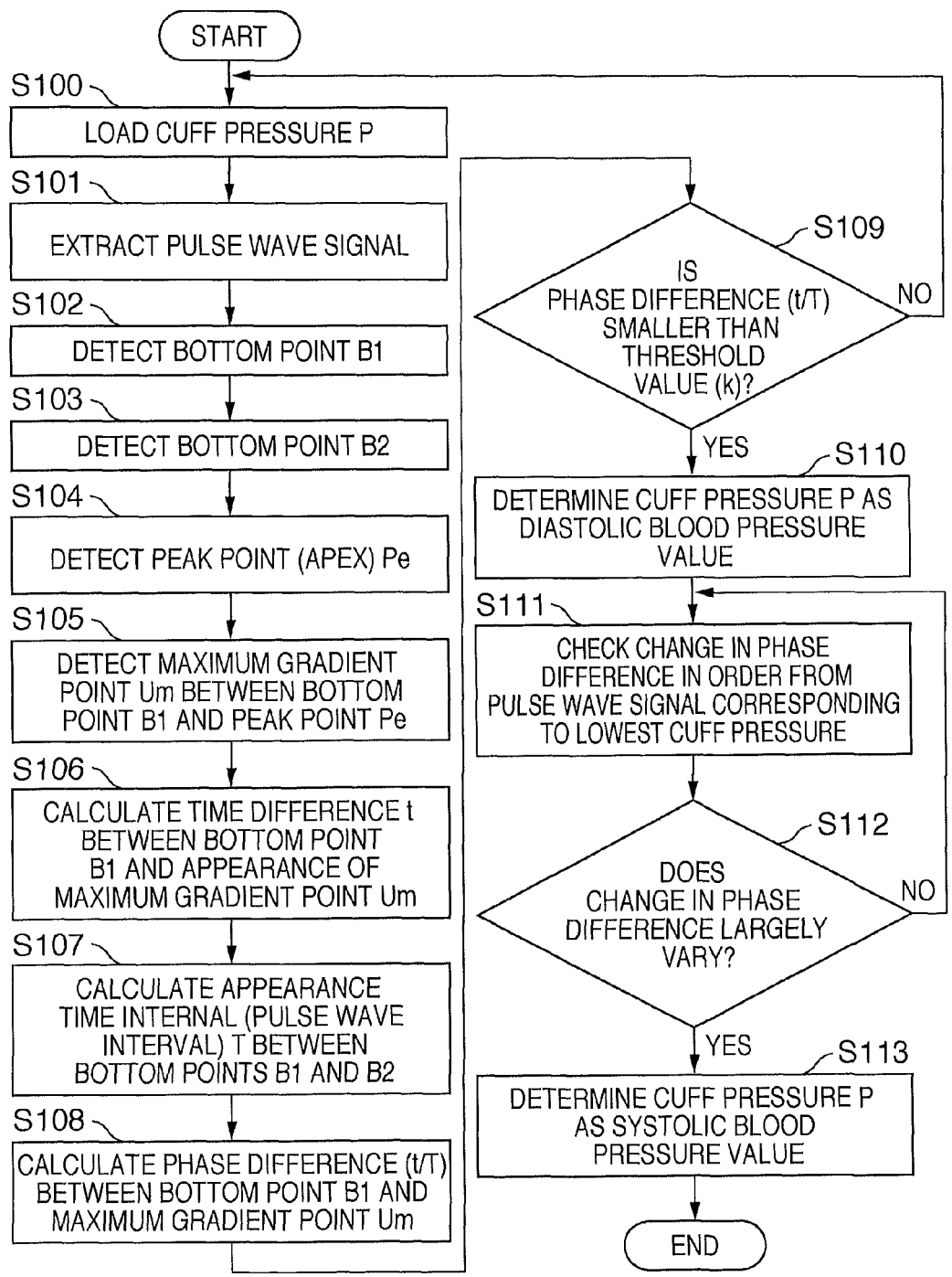
FIG. 10 is a detailed flowchart for determining the diastolic blood pressure value and systolic blood pressure value.

FIG. 10 is a detailed flowchart for determining the diastolic blood pressure value and systolic blood pressure value.

Even after the systolic blood pressure value is determined, a cuff pressure P is detected every predetermined time interval (every sampling time) (step S100), and the pulse wave signal (see FIGS. 7A and 7B) superposed on the cuff pressure is extracted (step S101). The successive bottom points B1 and B2 and the peak point Pe between them are detected from the pulse wave signal (steps S102, S103, and S104), and the point (maximum gradient point) Um having a maximum gradient is detected between the bottom point B1 (a bottom point produced ahead of the peak point) and the peak point Pe, that is, in the first half of the pulse wave signal (step S105). Subsequently, the time difference t between the bottom point B1 and the appearance of the point (maximum gradient point) Um having the maximum gradient is calculated (step S106). The time interval T between the bottom point B1 and the appearance of the bottom point B2 is calculated (step S107), and the phase difference (t/T) is calculated (step S108). Since the bottom point B2 is also the bottom point B1 of the next pulse wave signal, the time interval T is both the pulse wave interval and pulse period.

When this phase difference (t/T) becomes smaller than a predetermined threshold value k, the cuff pressure P at that point of time is determined as the diastolic blood pressure value (step S110). If the phase difference (t/T) is greater than or equal to the predetermined threshold value k, the same processing is performed on the next pulse wave signal to be superposed on the further reduced cuff pressure, and the diastolic blood pressure value is determined.

After the diastolic blood pressure is determined, the changes (differences) in phase difference are checked in order from a pulse wave signal corresponding to the lowest cuff pressure (steps S111 and S112). If a point at which the change in phase difference largely varies is found, the cuff pressure P corresponding to the point is determined as the systolic blood pressure value (step S113).

The operation has been explained by taking, for example, a combination of (diastolic blood pressure value determination 1) and (systolic blood pressure value determination 1) disclosed in <Determination of Blood Pressure Values>. However, the operation may also be executed based on another combination of the diastolic blood pressure value determination method and systolic blood pressure value determination method. Especially when combining a plurality of determination methods for each of the diastolic blood pressure value and systolic blood pressure value, the blood pressure values can be derived more accurately.

<Examples of Screen Display>

As described previously, the LCD 10 displays a graph as the basis of blood pressure determination as well. FIGS. 11A and 11B are views showing examples of the graph displayed on the LCD.

FIG. 11A is a view showing a two-dimensional graph in which the time is plotted on the abscissa (X-axis) direction, and the pulse wave amplitude is plotted on the ordinate (Y-axis) direction. Note that in FIG. 11A, the coordinates are distributed based on the bottom point. More specifically, the bottom point is (x,y)=(200,0). Note also that FIG. 11A shows an example when the systolic blood pressure value is close to 155 mmHg. Furthermore, it is favorable to display, on each graph, the cuff pressure value detected when the corresponding pulse wave signal is obtained, together with the corresponding pulse wave signal.

The display range of the two-dimensional graph is desirably the pulse wave signal of one period in the abscissa (X-axis) direction. However, it is also possible to display the pulse wave signal of a plurality of periods. Although a preset pulse wave amplitude can be displayed on the ordinate (Y-axis) direction, the scale of the display may also be changed as shown in FIGS. 11A and 11B. This arrangement has the advantage that the measurer can readily confirm the shape of a one-period pulse wave.

It is also possible to display the pulse wave signal based on the components corresponding to the signal such that the components can be identified. For example, as shown in FIG. 11B, it is preferable to display the W1-B component (X axis: 200 to 300) and the W1-A component (the rest) by different marks. When the LCD 10 is capable of color display, these components can also be displayed in different colors. The display like this allows the user to readily determine the reliability of the blood pressure value displayed in step S13. That is, the user can easily make the determination, in the displayed two-dimensional graph, based on the presence/absence of the W1-A component in the portion of the cuff pressure corresponding to the blood pressure value displayed in step S13.

Figure 12:
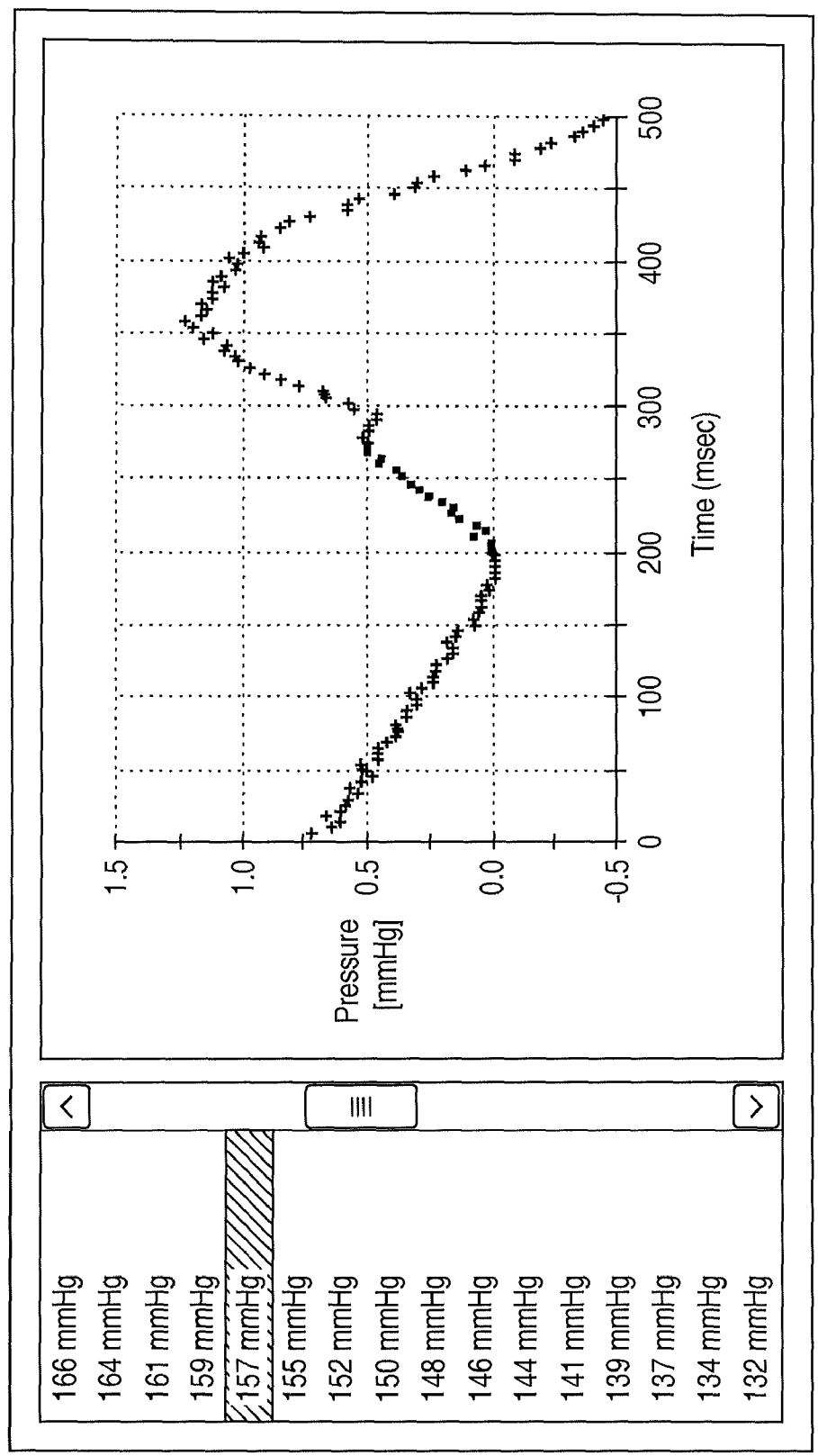
FIG. 12 is a view showing another example of the graph displayed on the LCD (data list display)

Furthermore, the device may also have a function of storing the measurement data of the pulse wave signal in a storage unit (not shown), so that the data can be displayed after the measurement in response to a user's operation. For example, as shown in FIG. 12, a data list in which a one-period pulse wave signal is associated with a corresponding cuff pressure can be generated. With this arrangement, the user can select the value of "cuff pressure" via an operation unit (not shown), and display the shape of a one-period pulse wave signal corresponding to the cuff pressure.

Figure 13:
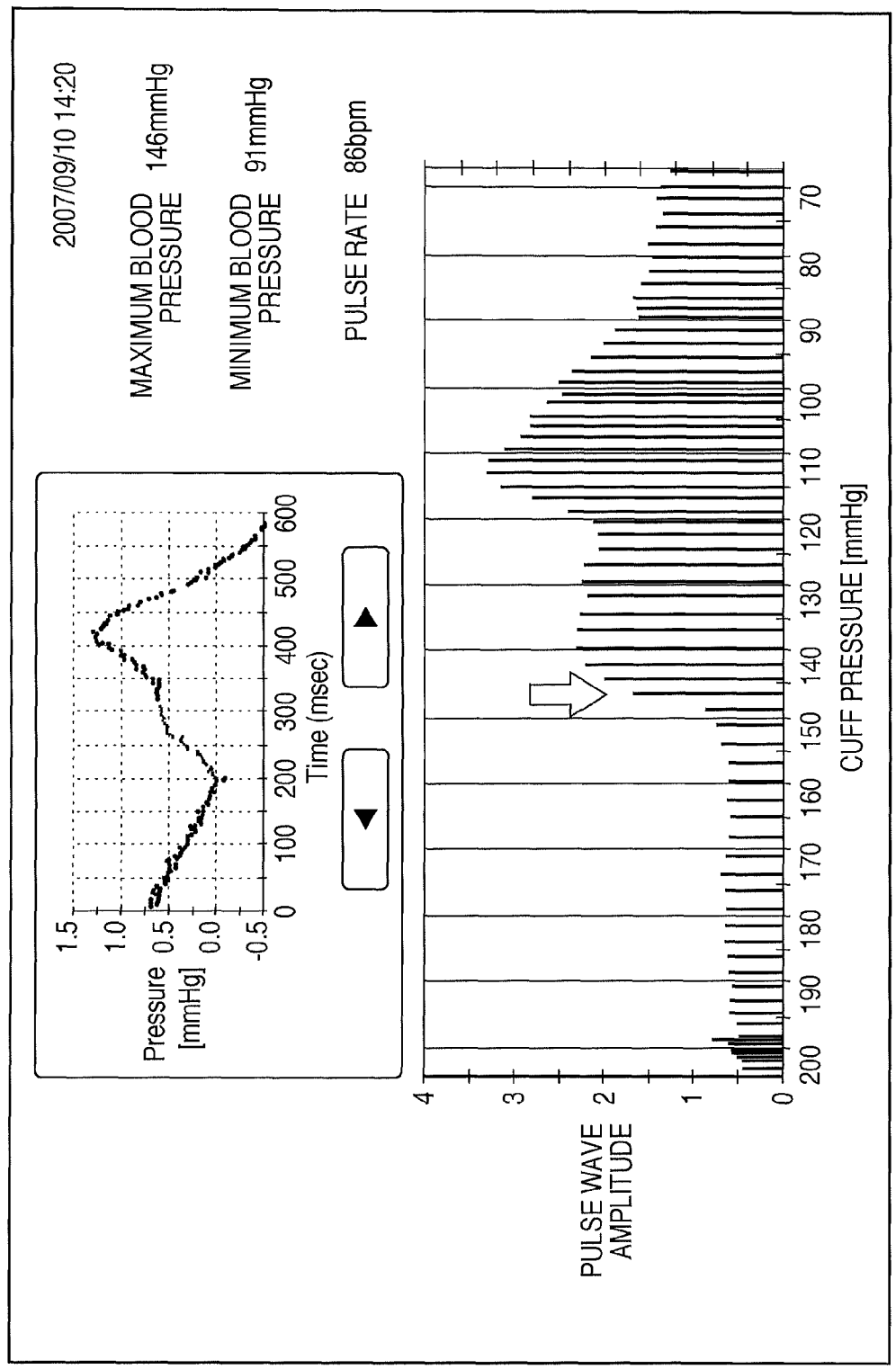
FIG. 13 is a view showing still another example of the graph displayed on the LCD (animation display)

It is also possible to successively display one-period pulse wave signals (by animation display) in the direction of descending order of cuff pressure, based on data stored in a storage unit (not shown). In this case, as shown in FIG. 13, it is favorable to display time-series data of the pulse wave amplitude detected when the pulse wave signal is acquired together with the corresponding pulse wave signal. Note that in FIG. 13, an animation display portion is positioned in the upper left corner of the screen, and the pulse wave amplitude time-series data is displayed in the lower portion of the screen. An arrow "1" indicates the position of the one-period pulse wave signal currently displayed in the animation display portion, on the pulse wave amplitude time-series data. In addition, the blood pressure values and pulse rate corresponding to the measurement are displayed in the upper right corner of the screen.

As has been explained above, the blood pressure measurement device according to the first embodiment determines the blood pressure values (the systolic blood pressure value and diastolic blood pressure value) based on not a statistical method but the change in shape of a pulse wave signal (one-period pulse wave signal). In addition, the pulse wave signal used in the blood pressure measurement is displayed on the LCD screen so that the user can confirm, together with the blood pressure values. With this configuration, the user can objectively determine whether the derived blood pressure values are appropriate.

This makes it possible to improve the objectivity, understanding, and reliability of blood pressure measurement. It is also possible to obtain information of, for example, the degree of arrhythmia, the degree of artifact caused by body motion or the like, or the difference between pulse wave magnitudes caused by individual differences, by displaying the amplitude of Korotkoff sounds detected during measurement or the pressure difference from the bottom to the maximum change point of the pulse wave. Therefore, the measurer can be notified of more information than that of the conventional sphygmomanometer that displays only numerical values. Consequently, information currently being measured can be provided in addition to the reliability of the measurement. Since this notifies the user of the necessity of remeasurement, highly reliable blood pressure values can be provided. In addition, it is possible to provide patient information such as arrhythmia or blood pressure fluctuation related to a therapy, and use the information in the therapy.

Note that the first embodiment has been explained by taking, for example, a blood pressure measurement device using the double cuff method obtained by improving the oscillometric method.

(Modification)

A modification will be explained below by taking, for example, a blood pressure measurement device using the triple cuff method obtained by further improving the double cuff method. Note that the arrangement and operation of the device except for the cuff are the same as those of the first embodiment, so a repetitive explanation will be omitted. In the following description, effects obtained by the use of a triple cuff will mainly be explained.

Figure 4:
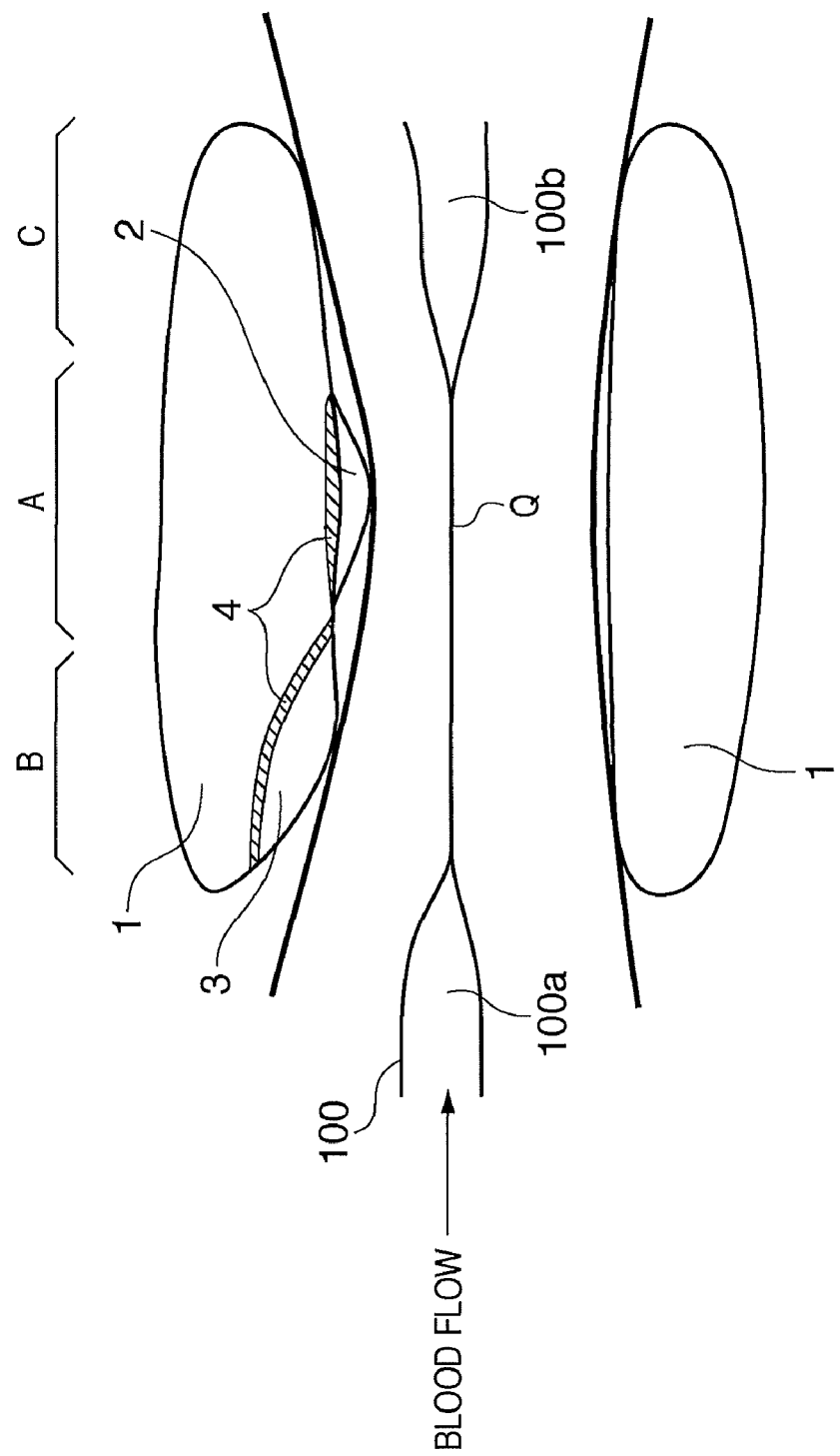
FIG. 4 is a sectional view in the longitudinal direction of a cuff (triple cuff) of a blood pressure measurement device according to a modification.

FIG. 4 is a sectional view in the longitudinal direction of a cuff (triple cuff) of the blood pressure measurement device according to the modification. The cuff according to this modification is a triple cuff including a large cuff 1 for blocking a blood vessel, a small cuff 2 for detecting a pulse wave, and a sub cuff 3 formed in an upstream portion. Dampers 4 for reducing the propagation of vibration are arranged between the large cuff 1 and small cuff 2, and between the large cuff 1 and sub cuff 3. The large cuff 1 and sub cuff 3 are connected to each other via a fluid resistance, and then aerially connected to a pressure sensor 5. Note that FIG. 4 shows the way the pressurized large cuff 1 for blocking a blood vessel blocks a portion Q of a blood vessel 100, thereby suppressing a blood flow from an upstream side 100a to a downstream side 100b.

As explained in the first embodiment, the pulse wave signal to be superposed on the cuff pressure, which is detected by the small cuff 2 for detecting a pulse wave, is divided into a component W1 (to be referred to as a W1 component hereinafter) resulting from a direct pressure change (blood vessel internal volume change) caused by a blood flow output from the upstream side of the cuff, and a component W2 (to be referred to as a W2 component hereinafter) resulting from a pressure change (blood vessel internal volume change) caused by the reflection from a blood vessel downstream of the cuff. The W1 component can be divided into three components, that is, W1-A, W1-B, and W1-C.

The sub cuff 3 has the effect of suppressing the W1-B component resulting from a blood vessel internal volume change caused by the blood flowing below a cuff upstream portion B, by compensating for the cuff-edge effect of the large cuff 1. FIG. 14A is a view showing a one-period pulse wave signal obtained by the double cuff. FIG. 14B is a view showing a one-period pulse wave signal obtained by the triple cuff. As shown in FIGS. 14A and 14B, in the pulse wave signal obtained by the triple cuff, the W1-B component is largely reduced, and as a consequence the W1-A component is detected more clearly. This makes it possible to more clearly detect the W1-A and W1-C components most important in the determination of the blood pressure value. Consequently, it is possible to more accurately derive "the phase difference" or "the displacement (of the amplitude value)" to be used in the determination of the blood pressure value.

As explained above, the blood pressure measurement device according to the modification can accurately acquire a pulse wave signal important in blood pressure determination. This makes it possible to derive more accurate blood pressure values (the systolic blood pressure value and diastolic blood pressure value). It is also possible to provide the user with accurate data indicating whether the derived blood pressure values are appropriate.

The present invention is not limited to the above-mentioned embodiments, and can variously be changed and modified without departing from the spirit and scope of the invention. Therefore, to apprise the public of the scope of the present invention, the following claims are made.

The invention claimed is:

1. A blood pressure measurement device comprising:
   a cuff adapted to press a blood pressure measurement portion, wherein said cuff includes a large cuff for blocking a blood vessel, and a small cuff for detecting a pulse wave, wherein said large cuff and said small cuff are connected via a fluid resistance;
   a pressure control unit adapted to pressurize or depressurize an interior of said large cuff;
   a pressure sensor adapted to sense an internal pressure of said small cuff;
   a pulse wave signal extracting unit adapted to extract time-series data of a pulse wave signal superposed on the cuff internal pressure sensed by said pressure sensor, in a process in which said pressure control unit pressurizes or depressurizes said large cuff; and
   a blood pressure determination unit adapted to determine a diastolic blood pressure value and a systolic blood pressure value based on the extracted pulse wave signal time-series data;
   a display unit adapted to display a pulse waveform corresponding to a pulse wave signal of at least one period, together with a value of a cuff internal pressure corresponding to the pulse wave signal;
   wherein the diastolic blood pressure value is determined based on (i) the cuff pressure when the phase difference between the bottom point produced ahead of the peak point of the pulse wave signal and the appearance of the maximum gradient point is smaller than a first predetermined threshold value, or (ii) the cuff pressure when the displacement of the bottom point produced ahead of or behind the peak point of the pulse wave signal from the maximum gradient point is smaller than a second predetermined value; and
   wherein the systolic blood pressure value is determined based on (iii) the cuff pressure value at a point where the phase difference between the bottom point produced ahead of the peak point of the pulse wave signal and the appearance of the maximum gradient point shows a large change having no value continuity when the phase difference for each pulse wave signal is checked in order from a pulse wave signal corresponding to the lowest cuff pressure, or (iv) the cuff pressure value at a point where the displacement of the bottom point produced ahead of or behind the peak point of the pulse wave signal from the maximum gradient point shows a large change having no value continuity when the displacement for each pulse wave signal is checked in order from a pulse wave signal corresponding to the lowest cuff pressure.

2. The blood pressure measurement device according to claim 1, further comprising:
   a list display unit adapted to display, in a form of a list for each period, each of a plurality of one-period pulse wave signals contained in the extracted pulse wave signal time-series data; and
   a selecting unit adapted to select one of the plurality of one-period pulse wave signals displayed in the form of a list,
   wherein said display unit displays the one-period pulse wave signal selected by said selecting unit, together with a value of a cuff internal pressure corresponding to the one-period pulse wave signal.

3. The blood pressure measurement device according to claim 1, further comprising:
   a time-series display unit adapted to display the extracted pulse wave signal time-series data as a two-dimensional graph in which the cuff internal pressure is plotted on a first axis and time is plotted on a second axis; and
   a selecting unit adapted to select one time included in a period of the pulse wave signal time-series data displayed as the two-dimensional graph,
   wherein said display unit displays a one-period pulse wave signal corresponding to the time selected by said selecting unit, together with a value of a cuff internal pressure corresponding to the one-period pulse wave signal.

4. The blood pressure measurement device according to claim 1, wherein said display unit updates and displays, every pre-designated time interval, a pulse waveform corresponding to a pulse wave signal of latest N periods (N is a natural number) contained in the pulse wave signal time-series data extracted by said pulse wave signal extracting unit, together with a value of a cuff internal pressure corresponding to the pulse wave signal.

5. The blood pressure measurement device according to claim 1, wherein said pulse wave signal extracting unit is configured to provide a temporal resolution of the pulse wave signal time-series data of not less than 250 Hz.

6. A control method of a blood pressure measurement device comprising a cuff configured to press a blood pressure measurement portion, wherein the cuff includes a large cuff for blocking a blood vessel and a small cuff for detecting a pulse wave, wherein the large cuff and the small cuff are connected via fluid resistance, a pressure control unit which pressurizes or depressurizes an interior of the large cuff, and a pressure sensor which senses an internal pressure of the small cuff, comprising:
   extracting time-series data of a pulse wave signal superposed on a cuff internal pressure sensed by the pressure sensor, while the pressure control unit is pressurizing or depressurizing the large cuff;
   determining a diastolic blood pressure value and a systolic blood pressure value based on the extracted pulse wave signal time-series data; and
   displaying a pulse waveform corresponding to a pulse wave signal of at least one period, together with a value of a cuff internal pressure corresponding to the pulse wave signal;
   wherein the diastolic blood pressure value is determined based on (i) the cuff pressure when the phase difference between the bottom point produced ahead of the peak point of the pulse wave signal and the appearance of the maximum gradient point is smaller than a first predetermined threshold value, or (ii) the cuff pressure when the displacement of the bottom point produced ahead of or behind the peak point of the pulse wave signal from the maximum gradient point is smaller than a second predetermined value; and
   wherein the systolic blood pressure value is determined based on (iii) the cuff pressure value at a point where the phase difference between the bottom point produced ahead of the peak point of the pulse wave signal and the appearance of the maximum gradient point shows a large change having no value continuity when the phase difference for each pulse wave signal is checked in order from a pulse wave signal corresponding to the lowest cuff pressure, or (iv) the cuff pressure value at a point where the displacement of the bottom point produced ahead of or behind the peak point of the pulse wave signal from the maximum gradient point shows a large change having no value continuity when the displacement for each pulse wave signal is checked in order from a pulse wave signal corresponding to the lowest cuff pressure.

* * * * *